I'm Patent Number: 5,298,618
Date of Patent: Mar. 29, 1994

United States Patent [19]
Speranza et al.

[54] MACROCYCLIC OXAMIDES

[75] Inventors: George P. Speranza, Austin; Donald H. Champion, Pflugerville; Martin J. Plishka, Austin, all of Tex.

[73] Assignee: Texaco Chemical Company, White Plains, N.Y.

[21] Appl. No.: 979,737

[22] Filed: Nov. 23, 1992

[51] Int. Cl.⁵ .......................................... C07D 273/08
[52] U.S. Cl. .................................... 540/454; 540/460
[58] Field of Search ........................... 540/454, 460

[56] References Cited

U.S. PATENT DOCUMENTS

| | | | |
|---|---|---|---|
| 2,156,300 | 5/1939 | Lippert et al. | 540/460 |
| 2,304,369 | 8/1940 | Morgan et al. | 540/460 |
| 4,870,172 | 8/1989 | Okami et al. | 540/460 |
| 4,900,818 | 2/1990 | Czech | 540/460 |

OTHER PUBLICATIONS

Vögtle et al., Liebigs. Ann. Chem., 1977, pp. 1702–1703.
Sun et al., Inorg. Chem., 25, 1986, 4780–4785.
C. J. Pedersen, "Cyclic Polyethers and Their Complexes with Metal Salts", *Journal of the American Chemistry Society*, vol. 89, No. 26, Dec. 20, 1967, pp. 7017–7036.
O. Vogl et al., "Polyoxamides. I. Polymerization of Cyclic Diamides", *Macromolecules*, vol. 1, No. 4, Jul.–Aug., 1968, pp. 311–315.
O. Vogl et al., "Polyoxamides. II. Polymerization of Cyclic Diamides", *Macromolecules*, vol. 1, No. 4, Jul.–Aug. 1968, pp. 315–318.
K. E. Krakowiak et al., "Synthesis of Aza-Crown Ethers", *Chemical Reviews*, vol. 89, No. 4, 1989, pp. 929–972.
R. A. Lofquist, et al., "Hydrophilic Nylon for Improved Apparel Comfort", *Textile Research Journal*, Jun. 1985, pp. 325–333.
L. Z. Chung et al., "Block Copolyetheramides. II. Synthesis and Morphology of Nylon-6 Based Block Copolyetheramides", *J. Polym. Sci. Part A: Polym. Chem.*, vol. 30, 1992, pp. 951–953.

*Primary Examiner*—John M. Ford
*Assistant Examiner*—P. K. Sripada
*Attorney, Agent, or Firm*—Jack H. Park; James L. Bailey; David L. Mossman

[57] ABSTRACT

Macrocyclic oxamides may be made easily, in good yield and in one step by reacting an oxalic compound, such as oxalic acid or oxalic esters, with a diamine, where the amine groups are separated by at least five atoms. The oxalic compounds may include, but are not limited to such materials as dimethyl oxalate and diethyl oxalate. The diamines may include, but are not limited to such materials as alkylenediamines; polyalkylene glycol diamines; alkyl-bis-(aminoalkyl)amines; imino bis-(alkyl)amines; and N,N' bis-(aminoalkyl)-N,N'-dialkylalkylenediamines and bis-(aminoalkyl)piperazines; and mixtures thereof. The macrocyclic oxamides made by this process may be used to selectively separate metal ions from solution, or complexed together with a metal ion act as a catalyst.

7 Claims, No Drawings

MACROCYCLIC OXAMIDES

FIELD OF THE INVENTION

The invention relates to large organic ring structures and methods for making the same and, in one aspect, more particularly relates to macrocyclic oxamides and methods for making the same.

BACKGROUND OF THE INVENTION

Large organic ring structures are known materials useful as chelating agents for selective binding and extraction of cations and as antioxidants. A number of other uses are recited in the recent review article by K. E. Krakowiak, et al., "Synthesis of Aza-Crown Ethers," Chemical Reviews, Vol. 89, No. 4, 1989, pp. 929-972, including use as key intermediates in the synthesis of cryptands and other N-substituted ligands.

Unfortunately, previous routes to producing the diaza crown ethers are very tedious and expensive, as outlined in the K. E. Krakowiak, et al. article. This publication notes that diaza crown ethers can be prepared by several different routes, for example, reacting 1,2-bis(2-haloethoxy)ethane or triethylene glycol ditosylates with triethylene glycol diamine or bis-(tosylamides) followed by removal of the pendant tosyl groups, if required. Another route concerns reacting a secondary amine with a 1,2-bis(2-haloethoxy)ethane followed by removal of the pendant alkyl groups; or reacting triethylene glycol diamine with triglycolyl dichloride. A number of other methods are described.

C. J. Pedersen, "Cyclic Polyethers and Their Complexes with Metal Salts," Journal of American Chemical Society, Vol. 89, No. 26, Dec. 20, 1967, pp. 7017-7036, describes the synthesis of 33 cyclic polyethers, derived from aromatic vicinal diols and containing 9 to 60 atoms including 3 to 20 oxygen atoms in the ring. Some of the compounds were prepared in good yields without the use of a high-dilution technique. Fifteen of the compounds have been catalytically hydrogenated to the corresponding saturated cyclic polyethers. Many of those containing 5 to 10 oxygen atoms form stable complexes with some or all of the cations of: Li, Na, $NH_4$, $RNH_3$, K, Rb, Cs, Ag(I), Au(I), Ca, Sr, Ba, Cd, Hg(I), Hg(II), La(III), Tl(I), Ce(III) and Pb(II). Many of these complexes could be isolated in the crystalline form depending on the anion. They appeared to be salt-polyether complexes formed by ion-dipole interaction between the cation and the negatively charged oxygen atoms of the polyether ring. The stoichiometry of the complexes is one molecule of polyether per single ion regardless of the valence. Some of the polyethers, by complexing, solubilize inorganic compounds, such as potassium hydroxide and permanganate, in aromatic hydrocarbons.

The preparation of cyclic dioxamides has been studied in O. Vogl, et al., "Polyoxamides. I. Polymerization of Cyclic Diamides," Macromolecules, Vol. 1, No. 4, July-August, 1968, pp. 311-315. After reviewing all the methods available to them, they chose the high dilution method using oxalyl chloride and diamine. Even though the high dilution technique was used, their yields of cyclic oxamide were very low. Attempts to prepare the cyclics from ethyl (or methyl) oxalate and hexamethylenediamine hydrochloride directly failed. Also of interest is O. Vogl, et al., "Polyoxamides. II. Polymerization of Cyclic Diamides," Macromolecules, Vol. 1, No. 4, July-August, 1968, pp. 315-318.

Certain oxamides are set out in R. M. Izatt, et al., "Thermodynamic and Kinetic Data for Macrocycle Interaction with Cations and Anions," Chem. Rev., 1991, pp. 1721-1777, but the unique oxamides of the present invention are not set forth.

As may be seen by reviewing the above-noted preparations, macrocyclic oxamides prepared by conventional methods often require more than one step, high dilution conditions and more than one reagent. All of these considerations increase the cost of the produced cyclic oxamides. Note that the Pedersen article discusses the desirability of avoiding high dilution techniques; Vogl, et al. were unable to avoid it. It would be desirable if cyclic oxamides could be prepared by a one-step procedure which did not require high dilution.

SUMMARY OF THE INVENTION

Accordingly, it is an object of the present invention to provide a simplified one-step procedure for synthesizing macrocyclic oxamides from readily available chemicals.

It is another object of the present invention to provide a method for the preparation of macrocyclic oxamides that does not require high dilutions.

Another object of the invention is to provide a family of novel macrocyclic dioxamides.

In carrying out these and other objects of the invention, there is provided, in one form, macrocyclic oxamides made by the reaction of an oxalic compound selected from the group consisting of oxalic acid and oxalic esters, with a diamine where the amine groups are separated by at least five atoms.

DETAILED DESCRIPTION OF THE INVENTION

It has been discovered that macrocyclic oxamides may be made simply and in one step and good yield by reacting oxalic acids or esters thereof with diamines where the amine groups are seperated by at least five carbon atoms. Surprisingly, the preferred procedure can be carried out in one step without resorting to high dilution techniques. Given the teachings of Vogl, et al., described above, that oxamides are not produced in one step by reacting ethyl (or methyl) oxalate and hexamethylenediamine hydrochloride, the present inventive process is particularly unexpected. Yields up to about 90% or more are obtained. Ring sizes varied from those containing 9 to 30 atoms and even higher. Additionally, the reaction can be scaled to the preparation of large quantities of material.

The cyclic products are good hosts for metallic ions making them useful in procedures for separating and removing metals from solutions. It is anticipated that the metallic complexes using the novel macromonomer dioxamides of this invention would be useful as catalysts for organic reactions.

The process involves reacting an oxalic compound with a diamine where the amine groups are separated by at least five atoms at a temperature between about 20° and 200° C., at a pressure between subatmospheric and about 10 atm, and in a solvent selected from the group consisting of isopropanol, 2-ethylhexanol, diglyme, triglyme, methanol, ethanol, N-methylpyrrolidone, and the like. Isopropanol is a preferred solvent; it is relatively nontoxic and is low in cost. In short, the solvent should be one which is inert, i.e. does not react with the diamine or the oxalic compound. Preferably, the reaction temperature is between about 20 and about 180° C. while the pressure is preferably atmospheric. No catalyst is required for the inventive reaction. As will be evident, the molar ratio of oxalic compound to diamine will vary depending on the cyclic compound desired to be formed, although in most cases the molar ratio will be about 1:1.

The oxalic compound may be oxalic acid or an ester thereof. In one embodiment, the oxalic compound is defined by the formula:

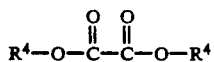

where $R^4$ is selected from the group consisting of hydrogen and $C_1$-$C_{12}$ straight or branched alkyl groups. In a preferred embodiment of the invention, the oxalic compound is selected from the group including, but not necessarily limited to, oxalic acid, dimethyl oxalate, diethyl oxalate, dipropyl oxalate, dibutyl oxalate and mixtures thereof.

As mentioned, the diamine preferably has two terminal primary amine groups separated by at least five other atoms. Suitable diamines may be represented by the formula:

$$H_2N-R-NH_2$$

where R is selected from the group consisting of:
(a) $C_5$-$C_{30}$ alkylene, preferably $C_6$-$C_{18}$, in one embodiment $C_{12}$-$C_{18}$ alkylene;

(b) 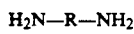

(c) 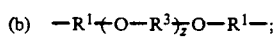

(d) 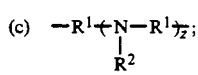

(e) 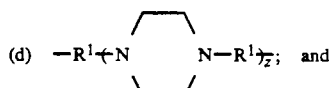

$R^1$ is independently $C_2$-$C_4$ straight or branched alkylene;
$R^2$ is independently H and $C_1$-$C_4$ straight or branched alkyl;
$R^3$ is independently $C_2$-$C_4$ straight or branched alkylene; and
z averages about 1-5. Defining z as averaging about 1-5 is meant that the diamines employed may have a distribution of different but similar molecules where the value of z would vary, e.g. where the value of z may range from 2-4, but the greatest single concentration would have z as 3, and the number average for the mixture would be about 3, though it may not be exactly 3; the exact value not necessarily being an integer. This definition applies to the values of x and y to be described later.

In one embodiment, the diamine is selected from the group including, but not necessarily limited to, alkylene diamines; polyalkylene glycol diamines; N-alkyl bis-(aminoalkyl)amines; imino bis-(alkylamines); and N,N'-bis-(aminoalkyl)-N,N'-dialkylalkylenediamines and bis-(aminoalkyl)-piperazines; and mixtures thereof. Specific examples of suitable diamines from these classes include, but are not necessarily limited to, tetraethylene glycol diamine; triethylene glycol diamine; tripropylene glycol diamine; bis-(aminoethyl)ether; bis-(aminopropyl)ether; 4,9-dioxa-1,12-diamine; hexaethylene glycol triamine (3,6,12,15-tetraoxa-9-azaheptadecane-1,17-diamine); dodecaneamine; bis-(aminopropyl)piperazine; methyl bis-(aminopropyl)amine; imino bis-(propylamine); and N,N'-bis-(aminopropyl)-N,N'-diisopropylethylenediamine.

It has been further discovered that residues or bottoms products obtained in the manufacture of triethylene glycol diamine (TEGDA) may be upgraded to form useful diamine reactants for the inventive process. TEGDA is a valuable chemical for the modification of nylon fibers and is also used as an epoxy curing agent; it is prepared by Texaco Chemical Company by aminating triethylene glycol and is sold under the tradename JEFFAMINE® EDR-148 amine. Higher boiling amines are also produced in the process.

Bottoms products from any process will vary somewhat, and thus are difficult to define with precision. Bottoms products from the preparation of TEGDA by the reduction of triethylene glycol with ammonia will vary depending upon the temperature and pressure which they are subjected to. Some of the bottoms products, which could be taken overhead, include triethylene glycol monoamine, TEGDA itself, and condensation products having structures such as the following:

$$NH_2-(CH_2CH_2O)_2CH_2CH_2-NH-(CH_2CH_2O)_2CH_2CH_2-NH_2$$

(hexaethylene glycol triamine; HEGTA); and $$NH_2-(CH_2CH_2O)_2CH_2CH_2-NH-(CH_2CH_2O)_2CH_2CH_2-OH$$

(hexaethylene glycol diamine);

It has been discovered that the value of these bottoms products may be upgraded by further aminating the hydroxyl containing materials such as hexaethylene glycol diamine in the presence of a metal catalyst containing nickel and optionally another transition metal. For example, the hexamethylene glycol diamine is further aminated to HEGTA according to reaction (I):

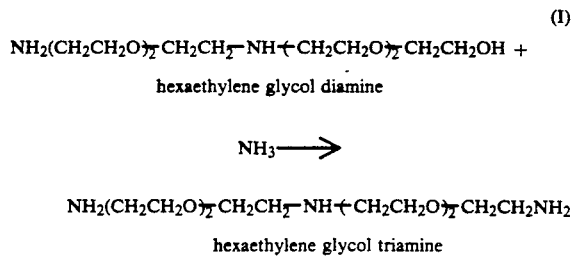

A similar situation exists with respect to tetraethylene glycol diamine (T4EGDA, JEFFAMINE® EDR-192) and the byproducts therefrom.

In one embodiment of the invention, the macrocyclic oxamides have the formula:

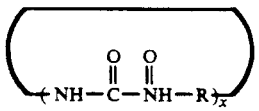

where x is 1 or 2;

R is independently selected from the group consisting of:
(a) $C_5-C_{30}$ alkylene, preferably $C_6-C_{18}$, in one embodiment $C_{12}-C_{18}$ alkylene;

(b) $-R^1+O-R^3\overline{)_z}O-R^1-$;

(c) $-R^1+N-R^1\overline{)_z}$;
　　　　$|$
　　　　$R^2$ (d) $-R^1+N\diagup\phantom{xx}\diagdown N-R^1\overline{)_z}$; and
　　　　　　$\diagdown\phantom{xx}\diagup$ (e) $-R^1-(O-R^3\overline{)_z}N-(R^3-O\overline{)_z}R^1-$; where
　　　　　　　　　　　$|$
　　　　　　　　　　$R^2$ $R^1$ is independently $C_2-C_4$ straight or branched alkylene;

$R^2$ is independently H and $C_1-C_4$ straight or branched alkyl;

$R^3$ is independently $C_2-C_4$ straight or branched alkylene; and z averages about 1–5.

The novel macrocyclic oxamides and the method for preparing them will now be further illustrated with certain examples, which are meant to illuminate but not necessarily limit the claimed invention. Product molecular weights were characterized with a Kratos magnetic sector mass spectrometer. A solid probe operating in an electron impact mode was employed.

EXAMPLE 1

To a 250 ml 3-necked flask equipped with a stirrer, thermometer, dropping funnel and Dean Stark trap were added 39 g. of tetraethylene glycol diamine (JEFFAMINE ® EDR-192) and 50 ml of isopropanol. Then 30 g. of diethyl oxalate in 50 ml of isopropanol was added over a 1.5 hour period. The contents were stirred for thirty minutes. A portion was taken out and allowed to stand overnight. A solid was collected which melted at 147°–150° C. It proved to be product (I) as shown in Chart 1 using analysis from Kratos mass spectrometer. However, at this point it was not realized that the cyclic material had been formed so the slurry was diluted further with isopropanol and methanol and added to 300 ml of 2-ethylhexanol at 180° C. The lower boiling alcohols were distilled out. The addition took place over a 3 hour period. A solid was filtered, washed with isopropanol and dried. The NMR analysis of this solid and that obtained by allowing the solid to settle from the isopropanol were identical. A total of 59 g. of solid were collected. The white solid had a molecular weight of 246.1216 which corresponds to product (I).

EXAMPLE 2

To a one liter four-necked flask equipped with two addition funnels, thermometer and stirrer was added 500 ml of isopropanol, and the isopropanol was heated to boiling. In one addition funnel was placed 29.2 g. of diethyl oxalate and 100 ml of isopropanol. In the second, the charge was 29.6 g. of triethylene glycol diamine (Jeffamine ® EDR-148) and 100 ml of isopropanol. The contents in the addition funnels were added simultaneously to the boiling isopropanol over a five hour period. A total of 38.8 g. of solid was obtained. A small amount was the 12-membered cyclic ring (II) in Chart 1, but the major portion was the 24-membered ring (III) in Chart 1.

Utility—The product of Example 2 (0.4971 g.) was added to 50 ml of a solution containing 10 ppm palladium and 1000 ppm calcium. The solution was stirred for 3 hours at room temperature and filtered through Whatman #1 paper. The resulting solution had 1.6 ppm Pd remaining for 84% removal. This shows the usefulness of the macrocyclic oxamide's selectivity to remove precious metals.

EXAMPLE 3

To a 500 ml 3-necked flask equipped with a stirrer, thermometer and two addition funnels was added 150 ml of isopropanol. One addition funnel contained 30 g. of diethyl oxalate and 100 ml of isopropanol. The second contained 40 g. of dodecanediamine (from E. I. Du Pont de Nemours, Colo.) and 100 ml of isopropanol. The contents were added over a 3.5 hour period keeping the pot temperature at 22°–29° C. The contents were stirred for eight hours at room temperature, filtered and dried. A total of 51.8 g of cyclic material melting at 227°–234° C. was obtained. The NMR indicated either a very high molecular weight polymer or a cyclic material. Kratos mass spectrum indicated a molecular weight of 254.2007 which corresponds to structure (IV) of Chart 1 with a molecular weight of 254.1994.

EXAMPLE 4

From bis-(aminoethyl)ether and diethyl oxalate using the technique described in Example 3 was obtained a minor amount of the nine-membered cyclic material (V) of Chart 1, but the bulk of the material was the 18-membered cyclic compound (VI). The measured molecular weight of 316.1378 corresponded closely to the actual molecular weight of 316.1382 for $C_{12}H_{20}N_4O_6$ for compound (VI).

EXAMPLE 5

From tripropylene glycol diamine having the formula:

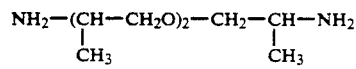

and diethyl oxalate and heating the isopropanol at 81°–82° C. was obtained the cyclic material (VII) of Chart I.

EXAMPLE 6

From bis-(aminopropyl)ethylene glycol and diethyl oxalate was obtained the cyclic material (VIII) of Chart 1 in high yield. The yield could not be determined, but it was high. Purity was not available

EXAMPLE 7

From 4,9-dioxa-1,12-dodecanediamine and diethyl oxalate was obtained compound (IX) of Chart 1 in good yield. Yield was about 80%; melting point was 158°–163° C.

EXAMPLE 8

The simultaneous addition of bis-(aminopropyl)piperazine with diethyl oxalate resulted in the cyclic ring (X) of Chart 1.

EXAMPLE 9

Into a one liter 3-necked flask equipped with a thermometer, two dropping funnels and a condenser was added 300 ml of isopropanol. The isopropanol was heated to boiling, and the two solutions from the dropping funnels were added over a 6.5 hour period. The two solutions were (a) 60 g. of diethyl oxalate (0.4 moles) and 150 ml of isopropanol and (b) 78 g. of Jeffamine EDR-192 (0.4 moles) and 132 ml of isopropanol. The product was filtered and dried. Mass spectrometry measurements showed some cyclic material (I), but mainly a ring with twice the molecular weight (XI). Sublimation yielded about 10% of the smaller ring structure (I).

EXAMPLE 10

When diethyl oxalate was heated with EDR-192 in the presence of potassium chloride, the main product was the smaller ring (I). From 30 g. of diethyl oxalate, 39 g. of EDR-192, 15.5 g. of potassium chloride and 582 ml of isopropanol was obtained 57.6 g. of solid which melted at 148°–150° C. The hard solid was difficult to filter and dry.

EXAMPLE 11

Into a two liter 3-necked flask equipped with a stirrer, condenser and two dropping funnels was charged 500 ml of isopropanol. One dropping funnel contained 58.4 g. of diethyl oxalate and 150 ml of isopropanol and the second held 59.2 g. of EDR-148 and 150 ml of isopropanol. The two solutions were added to boiling isopropanol at the same rate over a five hour period. The bulk of the material was the cyclic material involving two molecules of each of the starting material, compound (III). Sublimation indicated about 2% of cyclic compound (II) and the rest mainly (III). The yield of cyclic material was 80.8 g. or 96% of theoretical.

EXAMPLE 12

From methyl-bis-(aminopropyl)amine (43.5 g.) and diethyl oxalate (43.8 g.) using the technique in Example 11 above, was obtained 57.3 g. of solid. The product contained a small amount of the cyclic monomer (XII) but was mainly the larger ring (XIII). Titration for amine indicated 5.05 meq/g. (compared with theoretical of 5.03).

EXAMPLE 13

From imino-bis-propylamine and diethyl oxalate was obtained mainly the cyclic dimer (XIV) shown in Chart 1.

EXAMPLE 14

From diethyl oxalate and N,N'-bis-(aminopropyl)-N,N'-diisopropylethylenediamine was obtained some cyclic monomer; molecular weight indicated the structure of compound (XV). However, the main component was the cyclic dimer compound (XVI).

EXAMPLE 15

From diethyl oxalate and hexaethylene glycol triamine (3,6,12,15-tetraoxa-9-azaheptadecane-1,17-diamine) was obtained the cyclic amine (XVII) in good yield.

EXAMPLE 16

Recovery of Pt by Compound (III)

A 50 ppm solution of Pt/Co was used to test the removal capability of compound (III). A 0.404 g. sample was added to 50 ml of the test solution. After stirring for 30 minutes, filtering and analyzing, the Co level was the same, but the Pt level dropped from 41 ppm to 16 ppm. The test was repeated but stirring was continued for four hours. The Pt level dropped from 49 to 7 ppm.

EXAMPLE 17

Recovery of Potassium from Polypropylene Glycol

Compound (III) from Chart 1 in an amount of 0.001 moles was added to 20 g. of polypropylene glycol with a molecular weight of about 1950. The glycol solution contained 100 ppm potassium ion. The mixture was stirred for 3 hours and filtered. The filtrate contained 0.4 ppm potassium ion.

As demonstrated by Examples 16 and 17, the cyclic materials of this invention are good hosts for metallic ions and are thus useful for separating and removing metals from solutions. The exact amount of oxamide which may be used can readily be determined by one of skill in the art and any amount which removes metal ions is considered an effective amount. Generally, each oxamide molecule will remove about one metal ion as is customary in this art.

Many modifications may be made in the process of this invention without departing from the spirit and scope thereof which are defined only in the appended claims. For example, one skilled in the art may discover that certain reaction conditions or certain reactants or combinations thereof may give particularly advantageous results, such as giving predominantly the monomer vs. dimer of a particular macrocyclic oxamide.

CHART 1

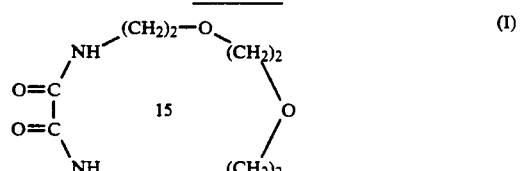

(I)

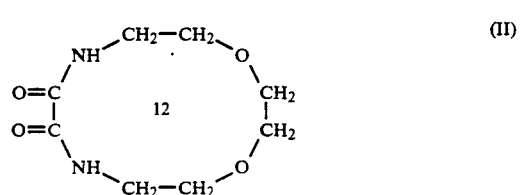

(II)

-continued
CHART 1
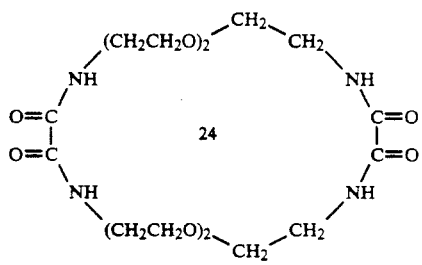 (III)
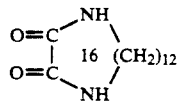 (IV)
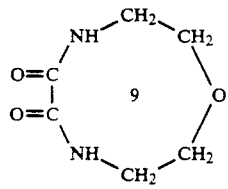 (V)
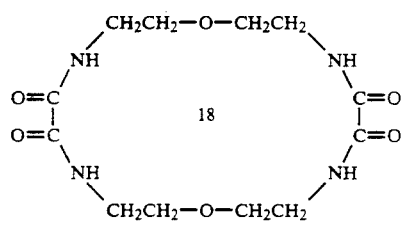 (VI)
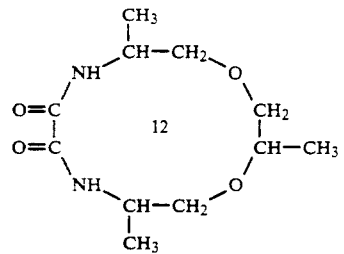 (VII)
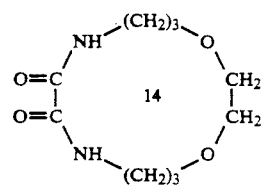 (VIII)
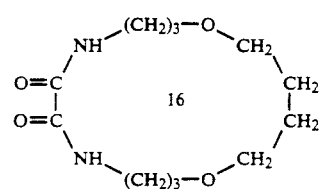 (IX)
-continued
CHART 1
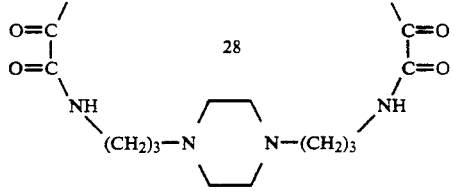 (X)
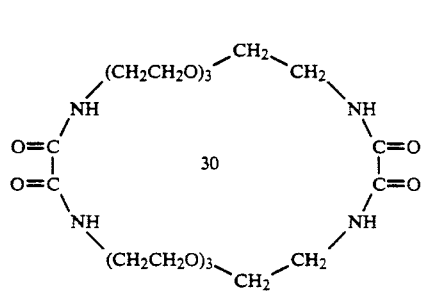 (XI)
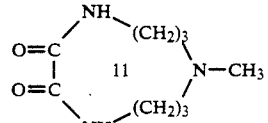 (XII)
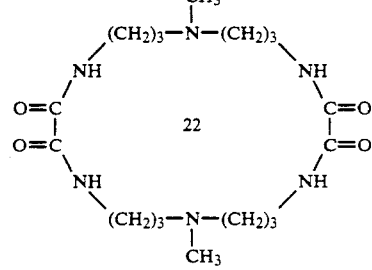 (XIII)
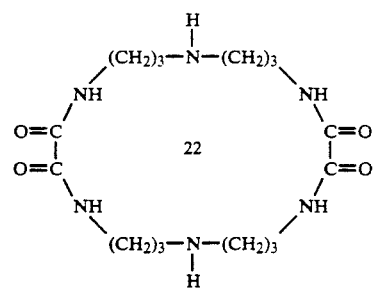 (XIV)
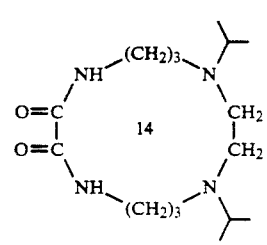 (XV)

-continued
CHART 1

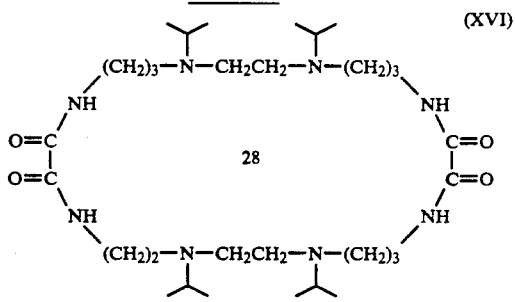

(XVI)

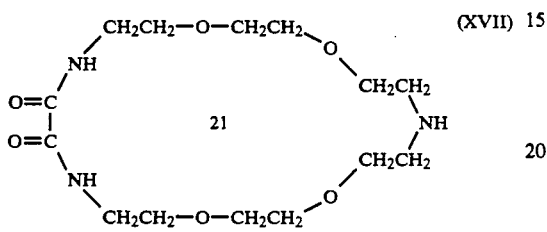

(XVII)

Note: Numbers in center of structure denote number of atoms in ring.

We claim:

1. Macrocyclic oxamides made by the reaction of an oxalic compound selected from the group consisting of oxalic acid and oxalic esters, with a diamine of the formula:

$$H_2N-R-NH_2$$

where R is selected from the group consisting of:

(a) 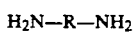

(b) 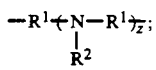

(c) 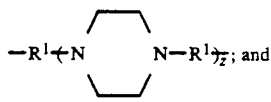

where $R^1$ is independently $C_2$-$C_4$ straight or branched alkylene;

$R^2$ is independently H and $C_1$-$C_4$ straight or branched alkyl;

$R^3$ is independently $C_2$-$C_4$ straight or branched alkylene; and z averages about 1-5.

2. The macrocyclic oxamides of claim 1 where the oxalic compound has the formula:

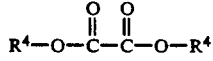

where $R^4$ is selected from the group consisting of hydrogen and $C_1$-$C_{12}$ straight or branched alkyl groups.

3. The macrocyclic oxamides of claim 1 where the oxalic compound is selected from the group consisting of dimethyl oxalate, diethyl oxalate, dipropyl oxalate, dibutyl oxalate and mixtures thereof.

4. Macrocyclic oxamides made by the reaction of an oxalic compound selected from the group consisting of oxalic acid and oxalic esters, with a diamine where the diamine is selected from the group consisting of alkyl-bis-(aminoalkyl)amines; imino-bis-alkylamines; and N,N'-bis-(aminoalkyl)-N,N'-dialkylalkylenediamines and bis-(aminoalkyl)piperazines.

5. The macrocyclic oxamides of claim 1 where the reaction is carried out at a temperature between about 20° and 200° C., at a pressure between subatmospheric and about 10 atm, and in a solvent selected from the group consisting of isopropanol, methanol, ethanol, 2-ethylhexanol, butanol, glycol ethers, diglyme and triglyme.

6. Macrocyclic oxamides having the formula:

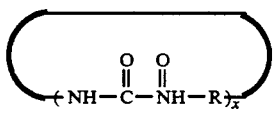

where x is 1 or 2;

R is independently selected from the group consisting of:

(a) 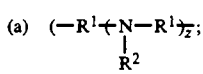

(b) 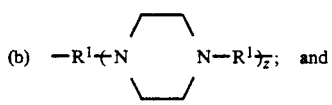

(c) 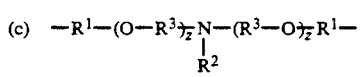

where $R^1$ is independently $C_2$-$C_4$ straight or branched alkylene;

$R^2$ is independently H and $C_1$-$C_4$ straight or branched alkyl;

$R^3$ is independently $C_2$-$C_4$ straight or branched alkylene; and z averages about 1-5.

7. Macrocyclic oxamides having the formula:

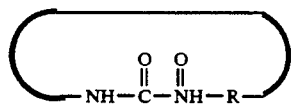

where R is independently selected from the group consisting of:

(a) $C_{12}$-$C_{18}$ alkylene;

(b) 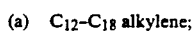

(c) 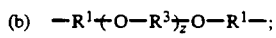 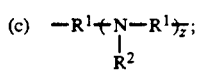

(d) 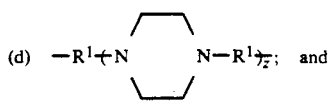

(e) 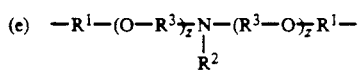
where
$R^1$ is independently $C_2$-$C_4$ straight or branched alkylene;
$R^2$ is independently H and $C_1$-$C_4$ straight or branched alkyl;
$R^3$ is independently $C_2$-$C_4$ straight or branched alkylene; and
z averages about 1-5.